United States Patent
Schuele

(10) Patent No.: US 10,743,758 B2
(45) Date of Patent: Aug. 18, 2020

(54) MULTIPLE DEPTH OPTICAL COHERENCE TOMOGRAPHY SYSTEM AND METHOD AND LASER EYE SURGERY SYSTEM INCORPORATING THE SAME

(71) Applicant: AMO Development, LLC, Santa Ana, CA (US)

(72) Inventor: Georg Schuele, Portola Valley, CA (US)

(73) Assignee: AMO Development, LLC, Santa Ana, CA (US)

(*) Notice: Subject to any disclaimer, the term of this patent is extended or adjusted under 35 U.S.C. 154(b) by 1054 days.

(21) Appl. No.: 14/970,921

(22) Filed: Dec. 16, 2015

(65) Prior Publication Data

US 2016/0278629 A1   Sep. 29, 2016

Related U.S. Application Data

(60) Provisional application No. 62/138,232, filed on Mar. 25, 2015.

(51) Int. Cl.
*A61B 3/10* (2006.01)
*A61B 3/12* (2006.01)
(Continued)

(52) U.S. Cl.
CPC ............ *A61B 3/102* (2013.01); *A61B 3/1005* (2013.01); *A61B 3/117* (2013.01); *A61B 3/1225* (2013.01);
(Continued)

(58) Field of Classification Search
CPC .......... G01N 21/14795; G01B 9/02091; G01B 9/02044; A61B 3/102; A61B 5/0066;
(Continued)

(56) References Cited

U.S. PATENT DOCUMENTS 5,720,894 A  2/1998 Neev et al.
5,957,915 A  9/1999 Trost
(Continued)

FOREIGN PATENT DOCUMENTS

EP  2044879 A1  4/2009
JP  H 02295536 A  12/1990
(Continued)

OTHER PUBLICATIONS

International Search Report and Written Opinion for Application No. PCT/US2015/065998, dated Mar. 18, 2016, 11 pages.
(Continued)

*Primary Examiner* — Baisakhi Roy
(74) *Attorney, Agent, or Firm* — Johnson & Johnson Surgical Vision, Inc.

(57) ABSTRACT

An OCT system for imaging multiple depth positions includes a light source, a sample arm and two or more reference arms. The sample arm propagates light to the object and directs object return light having a first return light beam from a first position and a second return light beam from a second position, the second return light having a dispersion level higher than the first return light beam by a dispersion difference amount. The first and second reference arms produce light beams having substantially the same dispersion as the first and second return light beams, respectively. The optical pathway combines all of the object return light and the reference light beams. An OCT detector measures the resulting interferogram. Imaging information is obtained for both the first position and the second position based on the dispersion difference amount.

20 Claims, 9 Drawing Sheets

(51) Int. Cl.
*A61F 9/008* (2006.01)
*A61B 3/117* (2006.01)
*G01N 21/47* (2006.01)
*A61B 5/00* (2006.01)
*G01B 9/02* (2006.01)

(52) U.S. Cl.
CPC ............ *A61F 9/008* (2013.01); *A61B 5/0066* (2013.01); *A61F 2009/0087* (2013.01); *A61F 2009/00851* (2013.01); *A61F 2009/00863* (2013.01); *G01B 9/02044* (2013.01); *G01B 9/02091* (2013.01); *G01N 21/4795* (2013.01)

(58) Field of Classification Search
CPC ... A61B 3/1005; A61B 3/1225; A61B 3/1208; A61B 3/125
See application file for complete search history.

(56) References Cited

U.S. PATENT DOCUMENTS

| | | | |
|---|---|---|---|
| 5,984,916 | A | 11/1999 | Lai |
| 6,019,472 | A | 2/2000 | Koester et al. |
| 6,454,761 | B1 | 9/2002 | Freedman |
| 7,655,002 | B2 | 2/2010 | Myers et al. |
| 7,717,907 | B2 | 5/2010 | Ruiz et al. |
| 7,800,759 | B2 | 9/2010 | Lai et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 2007/0081166 | A1* | 4/2007 | Brown ................. A61B 3/1005 356/479 |
| 2007/0263226 | A1* | 11/2007 | Kurtz ................. A61B 5/0059 356/492 |
| 2007/0291277 | A1* | 12/2007 | Everett ................. A61B 3/102 356/497 |
| 2011/0242487 | A1* | 10/2011 | Yuasa ................. A61B 3/102 351/206 |
| 2011/0261367 | A1* | 10/2011 | Gmitro ................. A61B 5/0066 356/479 |
| 2011/0319873 | A1 | 12/2011 | Raksi et al. |
| 2011/0319875 | A1 | 12/2011 | Loesel et al. |
| 2012/0065494 | A1* | 3/2012 | Gertner ................. A61B 5/055 600/411 |
| 2012/0200859 | A1 | 8/2012 | Breitenstein et al. |
| 2012/0253180 | A1* | 10/2012 | Emelianov ........... A61B 8/0841 600/424 |
| 2014/0139847 | A1* | 5/2014 | Brezinski ............... G01N 21/45 356/496 |

FOREIGN PATENT DOCUMENTS

| | | |
|---|---|---|
| JP | 2005527280 A | 9/2005 |
| JP | 2011104370 A | 6/2011 |
| JP | 2015503989 A | 2/2015 |
| WO | 2013081902 A1 | 6/2013 |

OTHER PUBLICATIONS

Hermann; B. et al., "Spectroscopic Measurements with Dispersion Encoded Full Range Frequency Domain Optical Coherence Tomography in Single and Multilayered Non-Scattering Phantoms", 2009, 17 (26), 24162-24174.

Hofer B., et al., "Dispersion Encoded Full Range Frequency Domain Optical Coherence Tomography," Optics Express, 2009, vol. 17 (1), pp. 7-24.

Hofer B., et al., "Fast Dispersion Encoded Full Range Optical Coherence Tomography for Retinal Imaging at 800 nm and 1060 nm," Optics Express, 2010, vol. 18 (5), pp. 4898-4919.

Leahy M., et al., "Multiple Reference Optical Coherence Tomography (MR-OCT) System," Proceeding of SPIE, 2013, vol. 8580, pp. 85800L-1-85800L-8.

Wang L., et al., "Highly Reproducible Swept-Source, Dispersion-Encoded Full-Range Biometry and Imaging of the Mouse Eye," Journal of Biomedical Optics, 2010, vol. 15 (4), pp. 046004-1-046004-6.

Zurauskas M., et al., "Frequency Multiplexed Long Range Swept Source Optical Coherence Tomography," Biomedical Optics Express, 2013, vol. 4 (6), pp. 778-788.

* cited by examiner

MULTIPLE DEPTH OPTICAL COHERENCE TOMOGRAPHY SYSTEM AND METHOD AND LASER EYE SURGERY SYSTEM INCORPORATING THE SAME

CROSS REFERENCE TO RELATED APPLICATIONS

This application is a non-provisional application and claims the benefit under 35 U.S.C. § 119(e) of U.S. Provisional Application Ser. No. 62/138,232, filed Mar. 25, 2015, which is incorporated herein in its entirety by reference.

BACKGROUND

Optical coherence tomography (OCT) is a noninvasive optical imaging technique which provides cross-sectional or three-dimensional images samples with an axial resolution of 1-15 μm. One of the main applications of OCT is in ophthalmology. Amongst the various known OCT systems, Fourier domain OCT (FD-OCT) is significantly faster than time domain OCT (TD-OCT) and has an improved signal to noise ratio (SNR).

But, FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, giving rise to mirror image artifacts and generally halving the useable range. This is referred to as the complex conjugate ambiguity. Another limitation is a sensitivity fall-off, which results in reduced sensitivity with increasing depth. Moreover, since the OCT's signal is derived only from backscattered photons, optical attenuation from absorption and scattering generally result in a useable imaging depth of less than 2 mm.

Several "full range" OCT techniques have been developed that eliminate the complex conjugate artifacts to effectively double the measurement range around the ZPD position. Recently, a Dispersion Encoded Full Range (DEFR) OCT procedure has been developed, which takes advantage of dispersion mismatch between a sample arm and a reference arm caused by a dispersive material in one arm that results in a broadening of signal peaks in z-space and makes it possible to eliminate complex terms. See B. Hofer, et al., Opt. Express 18, 4898-4919 (2010).

These so-called full range OCT techniques, however, result in useable imaging depths of about 4 mm. The average axial length of the adult human eye is about 24 mm. Thus, ophthalmic clinics must use three or more separate OCT measurements for: 1) imaging the retina, 2) imaging the anterior eye, and 3) measuring the axial eye length.

As a result of these shortcomings, there is a need for improved OCT systems and methods.

SUMMARY OF THE INVENTION

Accordingly, this disclosure provides embodiments of multiple depth OCT systems so as to obviate one or more problems due to limitations and disadvantages of the related art. One aspect of an embodiment of the present invention is a multiple depth OCT system which images two or more different positions in a sample in a single scan. Another aspect of the present invention is a multiple depth OCT system in which OCT return light from different depth positions separated by a dispersive medium in a sample have different dispersions, and each depth position is paired with a reference arm matching the respective path length and dispersions of the depth position, thereby providing a sample arm and reference arm matched at each depth position and encoded by their dispersion. The components of the resulting measured spectral interferogram can be separated based on their dispersion, thus providing image information at the multiple depth positions.

A multiple depth OCT system for imaging multiple depth positions in a sample comprises an OCT light source for producing a beam of light. A sample arm is configured to propagate the beam of light to the object and to direct an object return light comprising a first return light beam reflected from a first position in the object and a second return light beam reflected from a second position in the object, the second return light having a second dispersion level that is larger than a first dispersion level of the first return light beam by a dispersion difference amount. A first reference arm is configured to produce a first reference light beam at the first dispersion level and a second reference arm is configured produce a second reference light beam at the second dispersion level. The optical path is configured to combine all of the object return light, the first reference light beam and the second reference light beam and to direct the combined beams. An OCT detector is configured to measure a spectral interferogram based on the combined beams. Imaging information is obtained for both the first position and the second position based on the dispersion difference amount.

In one embodiment, a distance between the first position and the second position is preferably 5 mm or more. In another embodiment, a distance between the first position and the second position is 10 mm or more.

The object to be imaged is preferably an eye, including a human eye. Preferably, the first position to be imaged is at or near the anterior chamber of the eye. The second position is preferably located posterior to the anterior chamber of the eye. More preferably, the second position is located at or near the retina.

In one embodiment, the first reference arm comprises a partial mirror, the second reference arm comprises a mirror, a dispersive medium is between the partial mirror and the mirror, and an optical path length between the first position and the second position in the object is substantially the same as an optical path length between the reference arm partial mirror and the reference arm mirror.

In another embodiment, a laser surgical system comprises the multiple depth OCT system.

Another embodiment discloses a multiple depth OCT method for imaging an object, the OCT system comprising dividing a beam of light into a sample portion a reference portion. The method includes directing the sample portion along a sample arm optical path to the object and directing object return light back along the sample arm optical path, the object return light comprising a first return light beam reflected from a first position in the object and a second return light beam reflected from a second position in the object, the second return light having a second dispersion level that is larger than a first dispersion level of the first return light beam by a dispersion difference amount. It also includes dividing the reference portion between a reference arm configured to produce a first reference light beam at the first dispersion level and a second reference arm configured to produce a second reference light beam at the second dispersion level. The method includes a step of combining the object return light, the first reference light beam, and the second reference light beam and directing the combined beams to an OCT detector and measuring an interferogram based on the combined beams. Imaging information for both the first position and the second position is obtained based on the dispersion difference amount.

In one embodiment of the method, a distance between the first position and the second position is 5 mm or more. In another embodiment of the method, a distance between the first position and the second position is 10 mm or more.

The object to be imaged is preferably an eye, including a human eye. Preferably, the first position to be imaged is at or near the anterior chamber of the eye. The second position is preferably located posterior to the anterior chamber of the eye. More preferably, the second position is located at or near the retina.

In one embodiment, the first reference arm comprises a partial mirror, the second reference arm comprises a mirror, a dispersive medium is between the partial mirror and the mirror, and an optical path length between the first position and the second position in the object is substantially the same as an optical path length between the reference arm partial mirror and the reference arm mirror.

In another embodiment, a multiple depth OCT system for imaging multiple depth positions in a sample comprises an OCT light source for producing a beam of light. A sample arm is configured to propagate the beam of light to the object and to direct an object return light comprising a first return light beam reflected from a first position in the object and a second return light beam reflected from a second position in the object, the second return light having a second dispersion level that is larger than a first dispersion level of the first return light beam by a dispersion difference amount. The reference arm comprises a partial mirror, a mirror, and a dispersive medium between the partial mirror and the mirror. The partial mirror is configured to produce a first reference light beam having substantially the first dispersion level and the mirror configured to produce a second reference arm light beam at the second dispersion level.

A distance between the first position and the second position is preferably 5 mm or more. In another embodiment, a distance between the first position and the second position is 10 mm or more.

The object to be imaged is preferably an eye, including a human eye. Preferably, the first position to be imaged is at or near the anterior chamber of the eye. The second position is preferably located posterior to the anterior chamber of the eye. More preferably, the second position is located at or near the retina.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE FIGURES

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

The following description describes various embodiments of the present invention. For purposes of explanation, specific configurations and details are set forth so as to provide a thorough understanding of the embodiments. It will also, however, be apparent to one of ordinary skill in the art that embodiments of the present invention can be practiced without certain specific details. Further, to avoid obscuring the embodiment being described, various well-known features may be omitted or simplified in the description.

Figure 1:
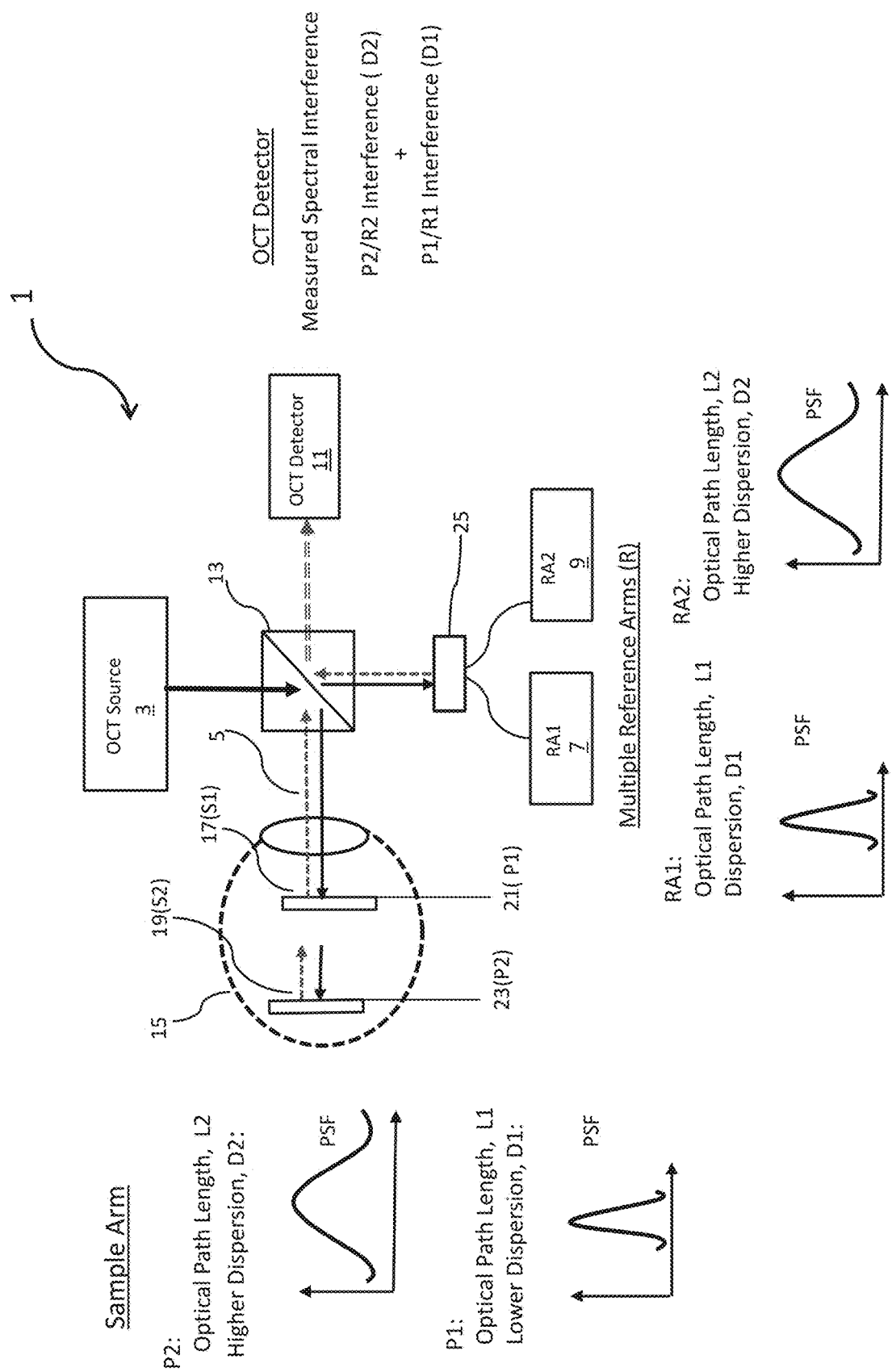
FIG. 1 is a schematic diagram of a multiple depth optical coherence tomography system.

Certain aspects and embodiments of the of the disclosed optical coherence tomography system and method may be understood by reference to FIG. 1. An optical coherence tomography (OCT) system 1 according to the present invention generally comprises an OCT light source 3, a sample arm 5, two or more reference arms 7 (RA1) and 9 (RA2), each reference arm having a different optical path length and a different dispersion characteristic, and an OCT detector 11 for detecting return light from the sample arm and the reference arms. The OCT system and method generally also comprise at least one beam splitter 13 that splits the light beam from the OCT light source into a sample arm and a reference arm.

In FIG. 1, a sample 15 to be imaged comprises two surfaces 17 (S1) and 19 (S2), surface 17 being at least partially reflective so that at least of a portion of an OCT light beam may pass therethrough. The two surfaces S1 and S2 are at different depth positions within the sample 15. Unless otherwise indicated, a depth position herein refers to a position in the sample along the direction of propagation of the OCT imaging light. The surfaces are separated at different depth positions within the sample by a predetermined distance. A dispersive medium is disposed between the surfaces S1 and S2 within the sample. The OCT system 1 provides structural information about sample 15 at two different depth positions 21 (P1), 23 (P2) within the sample. The first position, P1, is preferably at or near the first reflective surface, S1 and the second position, P2, is preferably at or near the second reflective surface, S2. For purposes of this application, a position P is near the reflective surface if less than 5 mm from that surface, or alternatively, less than 4 mm from that surface, or alternatively, less than 3 mm, less than 2 mm or less than 1 mm from the surface.

Beam splitter 13 generally splits the OCT light source into a sample arm 5 and the reference arms 7, 9. The sample arm 5 comprises one or more optical elements that define a sample arm optical path configured to direct light from the beam splitter 13 to the sample 15 to be imaged and also to direct return light from the at least two different depth positions 21 (P1) and 23 (P2) within the object back along the sample arm optical path. The return light is subsequently directed to an OCT detector 11.

In many embodiments, the optical path length, L1, of the sample arm optical path at position P1 is the sum of the optical path length of the OCT light beam as it travels from the OCT light source to position 1 and the optical path length of the return light from P1 to OCT Detector 11. The optical path length, L2, of the sample arm optical path at position P2 is the sum of the optical path length of the OCT light beam as it travels from the OCT light source 3 to position 2 and the optical path length of the return light from position P2 to OCT detector 11. However, for many embodiments, the difference in optical path lengths, L2-L1, may be suitably approximated as twice the optical path length between P1 and P2.

Since a dispersive medium is disposed between positions P1 and P2, the OCT light beam incident at position P2 has a higher dispersion than the dispersion of the OCT beam incident at position P1. Further, the return light from position P2 is also dispersed by the dispersive medium as it traverses the distance from P2 to P1. Thus, the dispersion difference between the reflected light from P2 and the reflected light from P1 occurs over a distance that is twice the distance between P1 and P2. As a result, the return light from position P2, as it is combined with (i.e., superimposed on) the return light from position P1, exits the sample and proceeds along the sample arm optical path at a higher dispersion than the return light from position P1. A dispersion amount, D1, of the return light from position P1 is defined as a dispersion amount of the return light from position P1 at OCT detector 11. A dispersion amount, D2, of the return light from position P2 is defined as a dispersion amount of the return light from position P2 at OCT detector 11. This difference in the dispersion of the return light from positions P1 and P2, respectively, is illustrated graphically in FIG. 1 as a difference in the point spread functions (PSF) of the return light from positions P1 and P2. In many embodiments, the difference in the dispersion between positions P1 and P2, may be suitably approximated as twice the dispersion of a light beam caused by the dispersive medium between P1 and P2.

One aspect of many embodiments is the use of multiple reference arms 7, 9 one reference arm for each position within the object to be imaged. In many embodiments, a second or subsequent optical element 25 is used to divide OCT light beam further to yield two or more reference arm optical paths. The optical elements may be, for instance, a beam splitter or partial mirror. In FIG. 1, optical element 25 divides the OCT light beam into a first reference arm 7 (RA1) and a second reference arm 9 (RA2). A portion of the OCT light beam divided by beam splitter 13 then proceeds along reference arm 7 and a different portion then proceeds along reference arm 9. Each of reference arms 7 and 9 comprises optical elements defining a respective reference arm optical path configured to direct light from the beam splitter 13, beam splitter 25 and along the respective reference arm optical paths 7, 9, which are the re-combined and subsequently directed to an OCT detector 11.

A first reference arm 7 (RA1) corresponds to the sample at position P1, and a second reference arm (RA2) the Sample at position P2. According to many embodiments, a reference arm corresponds to a sample position within the object to be imaged if the optical path length and dispersion of the reference arm are the same or substantially the same as the optical path length and dispersion at the position to be imaged in the sample arm. The optical elements of each reference arm are thus configured to match the respective optical path length and dispersion to the corresponding sample arm optical path length and dispersion. Thus, in FIG. 1, reference arm RA1 corresponds to the sample arm at position P1 because the optical path length, L1 and dispersion, D1 are the same or substantially the same. Similarly, reference arm RA2 corresponds to the sample arm at position P2 because the optical path length, L2, and the dispersion, D2 are the same. As would be understood by the ordinarily skilled, the various reference arms may have shared optical elements. Here, the dispersion is substantially the same if a percent difference in a measured dispersion parameter is less than 10%, and alternatively, less than 5%, less than 4%, less than 3%, less than 2%, or less than 1%. A difference in optical path length between a sample arm and reference arm is substantially the same if, all other factors being equal, the difference is small enough to detect a spectral interference spectrum of the OCT light source.

Once the combined return light beams from each position with the sample and each reference arm are combined, they are directed to the OCT detector 11. OCT detector 11 detects (i.e., measures) a spectral interferogram resulting from the interference of the return light reflected from each position to be imaged, e.g., depth positions P1 and P2 in FIG. 1, as well as the light from each of the reference arms, RA1 and RA2. As shown in FIG. 1, the measured spectral interferogram includes a component spectral interferogram corresponding to a spectral interference between the return light from position P1 and the return light from the corresponding reference arm RA1, both having the lower dispersion, D1. Another component element of the measured spectral interferogram corresponds to a spectral interferogram between the return light from position P2 and the light from the corresponding reference arm RA2, both having the higher dispersion, D2. As is obvious to one ordinarily skilled, the described construction provides for a measured OCT spectral interferogram comprising component spectral interference spectra corresponding to each of the positions within the sample to be imaged, each component spectral interferogram being encoded according to their respective dispersion properties.

The OCT systems and methods of the present invention are generally FD-OCT (Fourier domain optical coherence tomography) systems, including either an SD-OCT (spectral domain optical coherence tomography) system or an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

The component spectral interferograms are separated from one another in the measured spectral interferogram based upon the difference in dispersion between the respective positions, P1 and P2 to be imaged. This may be accomplished by a modification of the Dispersion Encoded Full Range (DEFR) OCT procedure described and developed in B. Hermann, et al. "Spectroscopic measurements with dispersion encoded full range frequency domain optical coherence tomography in single- and multilayered non-scattering phantoms," Opt. Express 17, 24162-24174 (2009); B. Hofer et al., "Dispersion encoded full range frequency domain optical coherence tomography," Opt. Express 17, 7-24 (2009); B. Hofer, et al., "Fast dispersion encoded full range optical coherence tomography for retinal imaging at 800 nm and 1060 nm," Opt. Express 18, 4898-4919 (2010); and L. Wang, et al., "Highly reproducible swept-source, dispersion-encoded full-range biometry and imaging of the mouse eye," J. Biomed. Opt. 15, 046004 (2010), the entire contents of all of which are hereby incorporated by reference in their entirety.

In Dispersion Encoded Full Range (DEFR) OCT, a dispersion mismatch between a sample arm and a reference arm caused by a dispersive material in one arm results in a broadening of signal peaks in z-space. This dispersion mismatch is numerically compensated for in k-space before the inverse Fourier transform, thereby restoring the true signal components and broadening their complex conjugate mirror artifacts. Next, a peak detector reveals the true signal components and their mirror artifacts can be subsequently removed.

The DEFR algorithm introduces one iterative step into conventional OCT processing, the iterative step occurring between two conventional OCT processing steps. In a first convention step of OCT processing, the spectral data are corrected for detector background then linearized in k-space and spectrally shaped. In case of dispersion mismatch between the sample and reference arm, a corresponding phase shift is introduced to restore the resolution. In the second step of conventional FD OCT processing, the data are then Fourier transformed and displayed using only the amplitudes and logarithmic scaling. The DEFR algorithm is introduced iteratively in between these two processing steps by identifying the highest signals in the depth data and removing them from the spectral data. In one embodiment of DEFR, only one component was removed in each step, which could result in as many steps as sample data points, and was computationally expensive and time consuming. In another embodiment many component steps are removed in one step. In DEFR, a high dispersion between sample and reference arm ensures a large amplitude ratio between the true signals and the complex conjugate artifacts thereby reducing the number of necessary iteration steps. The DEFR iteration stops if all the complex conjugate artifacts are below the noise level.

The iterative DEFR algorithm requires two Fourier transforms for the subtraction of a single signal component. That is in each iteration, two Fourier transforms are needed to calculate from z-space to the complex conjugate spectrum in z-space again after application of a phase shift in k-space:

$$\mathcal{F}^{-1}(\mathcal{F}_{(c(z))}e^{\pm i2\phi(k)})(z)$$

where c(z) denotes the complex spectrum in z-space and $e^{-i2\phi(k)}$ is twice the (inverse) dispersive phase function caused by the dispersive material in the reference arm of the interferometer. Additionally, two further Fourier transforms are required to calculate from the complex conjugate spectrum in z-space to the 'original' spectrum in z-space after applying the opposite phase shift in k-space.

The DEFR algorithm can be modified for application to the multiple-depth imaging and, when done, may be referred to as Diffusion Encoded Multiple Depth (DEMD) OCT. Whereas in DEFR, a dispersion mismatch is introduced between the sample arm and reference arm, in DEMD, the reference arm and sample arm are dispersion matched, and the dispersion mismatch is between interference corresponding to position P1 and interference corresponding to position P2. In DEMD, a high dispersion between position P1 and position P2 results in a large amplitude ratio between the signals corresponding to position P1 and the signals corresponding to P2. The necessary dispersion to ensure a sufficiently large amplitude ration can be experimentally determined based on the sample. In ophthalmic indications, the vitreous humor has an index of refraction of 1.336. Preferably, the difference in dispersion between positions to be imaged (e.g., between position P1 and P2) should be dispersion caused by larger than the dispersion of the OCT light source caused by a 10 mm thickness of vitreous humor, or alternatively, a 16 mm thickness of vitreous humor, or alternatively a 20 mm thickness of vitreous humor.

Figure 6:
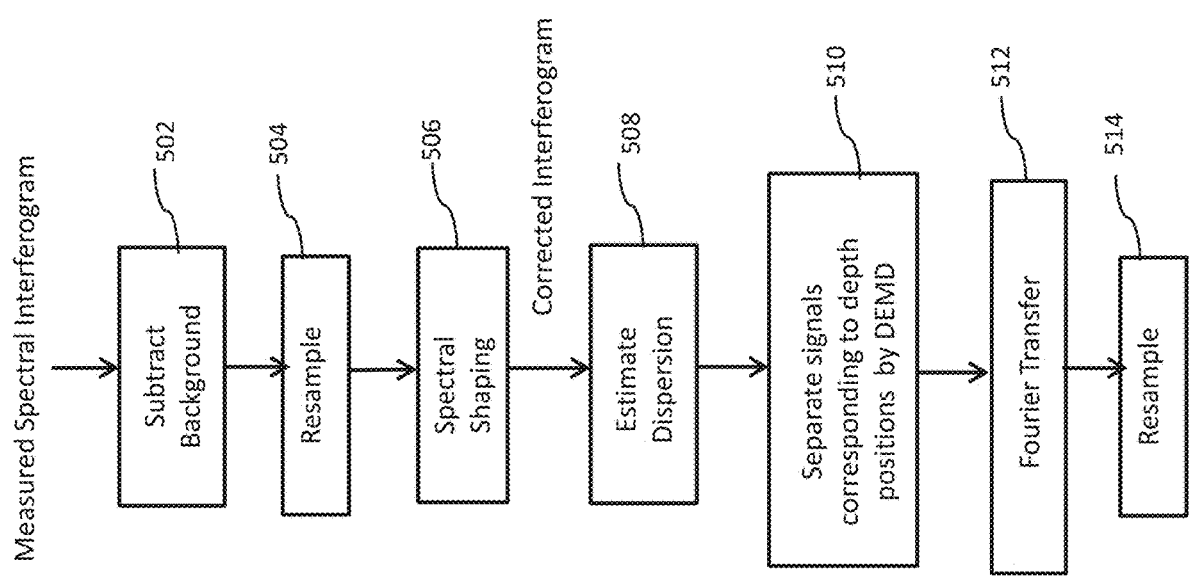
FIG. 6 is a flow chart of the spectral interferogram processing steps of a dispersion encoded multiple depth optical coherence tomography system.

FIG. 6 is a summary of the processing steps used in DEMD. First, at step 502, the measured spectral interferogram data are corrected for detector background (Step 502) then resampled (i.e., linearized in k-space) (Step 504) and spectrally shaped (Step 506). These steps are conventional in OCT data processing and are well within the skill of those ordinarily skilled in the art. These series of steps provide a corrected interferogram that is the basis for the remaining processing steps. At step 508, the dispersion mismatch between the sample arm at position P1 and the sample arm at position P2 is estimated. At step 510, the contribution from each signal corresponding to the each position in the sample to be imaged is separated by DEMD based on the dispersion difference between P1 and P2. Finally, the data are Fourier transformed (Step 512) and optionally displayed (Step 514) using the amplitudes and logarithmic scaling.

In DEMD, at Step 508, a frequency-dependent dispersive phase $\phi(k)$ must be estimated before the dispersive phase term $e^{-i\phi(k)}$ can be applied prior to inverse FFT. The frequency-dependent dispersive phase $\phi(k)$ can be estimated using information entropy of the spatial domain signal (on a linear scale) as a sharpness metric R(•). See Y. Yasuno, et al., "In vivo high-contrast imaging of deep posterior eye by 1-um swept source optical coherence tomography and scattering optical coherence angiography," Opt. Express 15, 6121-6139 (2007). Generally, it only necessary to determine parameters, $a_2$ and $a_3$, corresponding to the second and third order dispersion coefficients $$\phi(k_u) = \frac{1}{N-1}(a_2 u^2 + a_3 u^3)$$

For data from free-space interferometer measurements, several optical path length differences (OPDs) can be used to estimate dispersion. See B. Hofer et al., "Dispersion encoded full range frequency domain optical coherence tomography," Opt. Express 17, 7-24 (2009);

In DEMD, the corrected interferogram is first inverse Fourier transformed. A peak detector finds the strongest signal components in z-space and removes one or more of them from the spectrum. These removed signal components correspond to the signal components corresponding to position P1. Then, in order to recover the signal components corresponding to position P2, the Fourier transform is calculated and the dispersive phase, $e^{\pm i\phi(k)}$ due to the dispersion at position P2 is applied on the signal in k-space. Then, the phase adjusted spectrum in at position P2 in z-space is retrieved via inverse Fourier transform.

By decoding the signals at depth position P1 and depth position P2 in this manner, the OCT systems and methods described herein therefore provide for providing image information of a sample at multiple-depths within the sample in a single A-scan.

Figure 2:
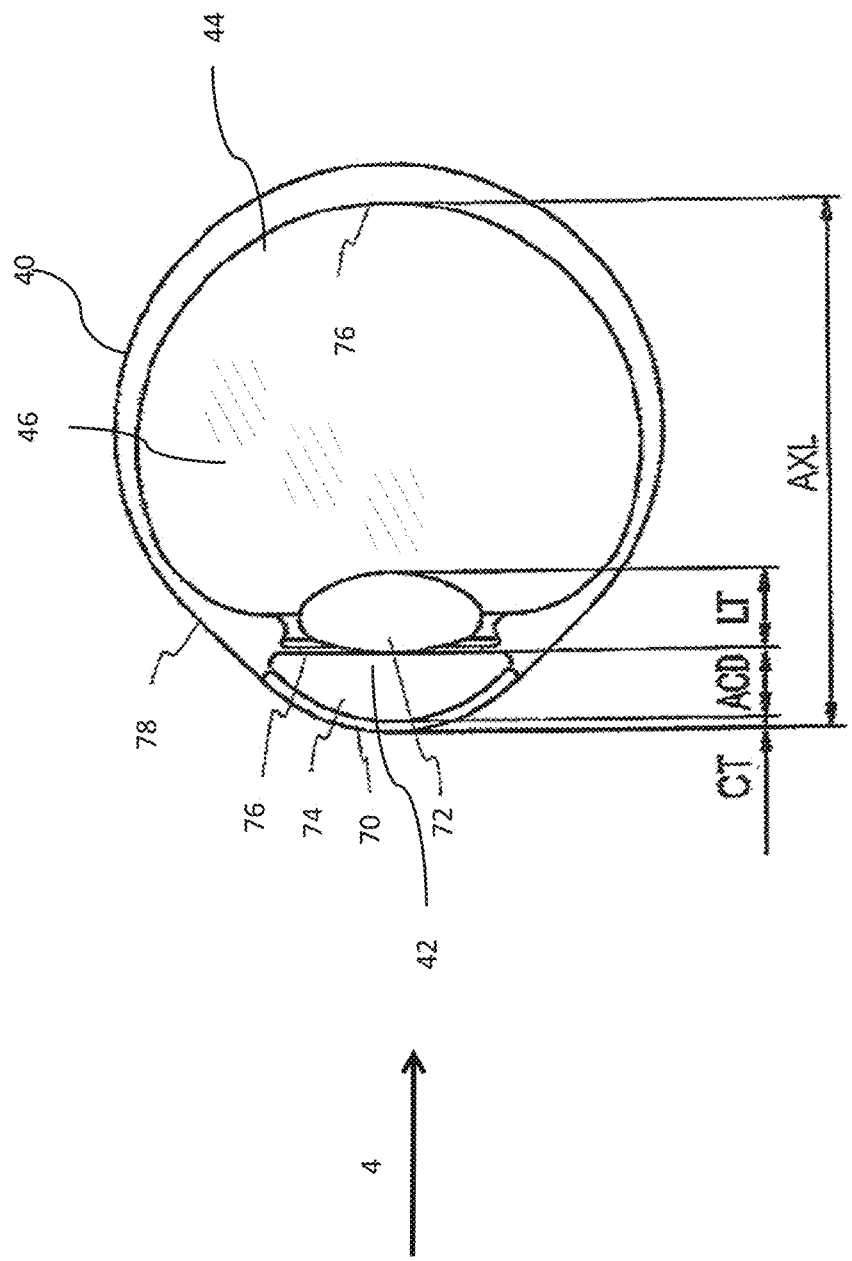
FIG. 2 is a schematic diagram of a human eye.

In particular preferred embodiments, the object to be imaged at multiple depths by the OCT system and method is an eye, preferably a human eye. FIG. 2 is a schematic drawing of a human eye 40. In many embodiments, a light beam from OCT light source 4 enters the eye from the left of FIG. 4, refracts into the cornea 70, passes through the anterior chamber 74, the iris 76 through the pupil, and reaches lens 72. After refracting into the lens, light passes through the vitreous chamber 46, and strikes the retina 76, which detects the light and converts it to an electric signal transmitted through the optic nerve to the brain (not shown). The vitreous chamber 46 contains the vitreous humor, a clear liquid disposed between the lens 72 and retina 76. As indicated in FIG. 2, cornea 70 has corneal thickness (CT), here considered as the distance between the anterior and posterior surfaces of the cornea. Anterior chamber 74 has anterior chamber depth (ACD), which is the distance between the anterior surface of the cornea and the anterior surface of the lens. Lens 72 has lens thickness (LT) which is the distance between the anterior and posterior surfaces of the lens. The eye has an axial length (AXL) which is the distance between the anterior surface of the cornea and the retina, where the image should focus.

The anterior chamber 46 is filled with aqueous humor, and optically communicates through the lens with the vitreous chamber, which occupies the posterior ⅘ or so of the eyeball and is filled with vitreous humor. The average adult eye has an ACD of about 3.15 mm, with a large variability between individuals. The average adult eye has an AXL of about 24 mm.

In many embodiments, the two or more positions to be imaged in the eye include a first position at or near the anterior surface of the lens and a second position at or near the retina. In some embodiments, the first position is located at about 0 to 7 mm, or alternatively, at 2 to 5 mm, or 3 to 4 mm within the adult human eye as measured from the anterior surface of the cornea to the retina along the axial length of the eye. The location of the first position may account for individual variation or for the different populations, such as children. In some embodiments, the second position is located from about 12 mm to the entire length (AXL) of the eye (e.g., 24 mm), alternatively at 15 mm to the entire length, and preferably 20 mm to the entire length within the adult human eye as measured from the anterior surface of the cornea to the retina along the axial length of the eye. The physical distance between the two positions to be imaged may be more than 5 mm, or alternatively, more than 7 mm, more than 10 mm, or more than 15, or more than 20 mm.

Figure 3:
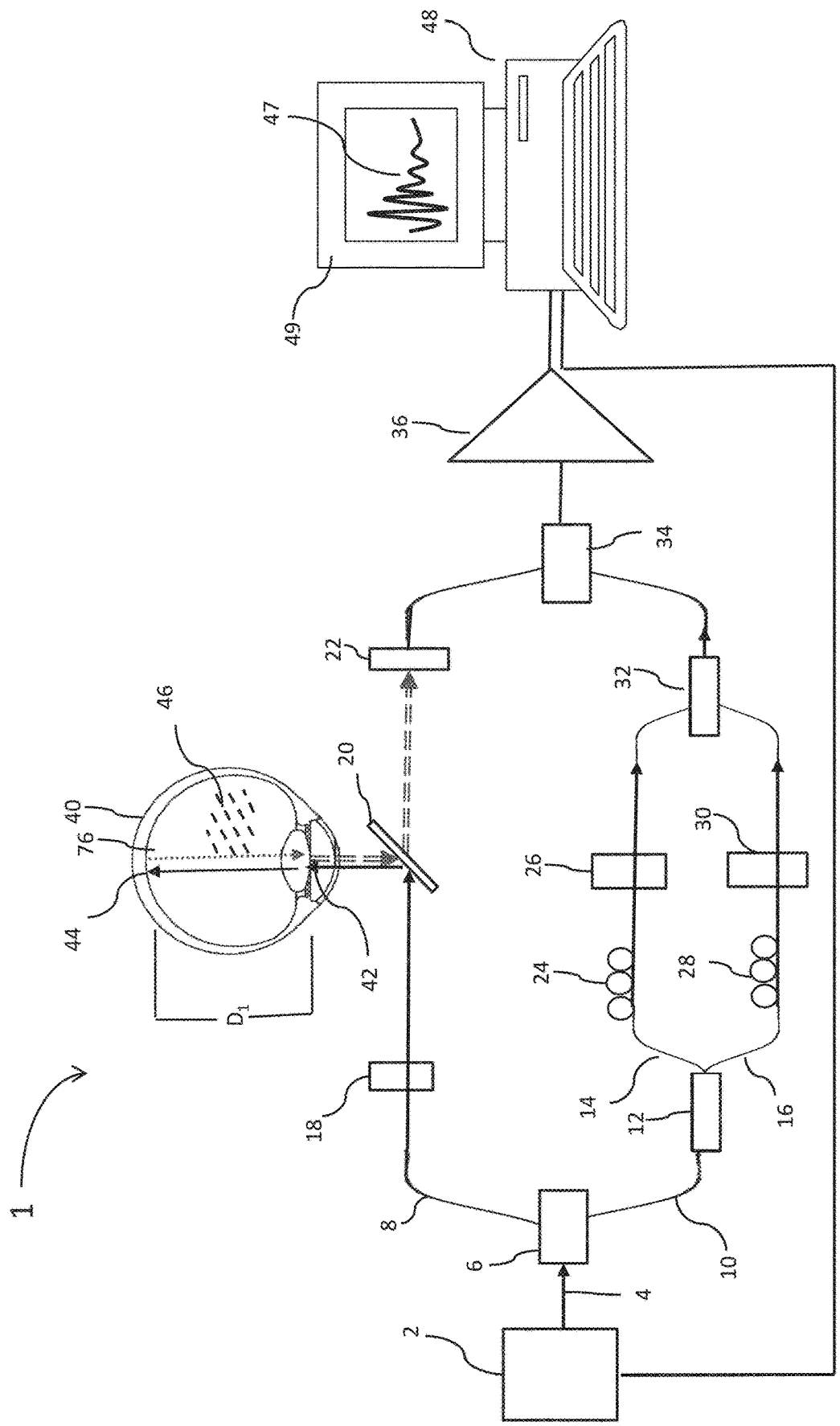
FIG. 3 is a schematic diagram of a second embodiment of a multiple depth optical coherence tomography system.

One embodiment of a system and method for multi-depth OCT is shown in FIG. 3 in the context of imaging an eye. In FIG. 3, an OCT light source 2 produces a light beam 4 that is divided by beam splitter 6 into a sample arm 8 and a reference arm 10.

The nature of the OCT light source and the wavelengths of the light beam are not particularly limited but the selected wavelength of the light beam should be selected so that it is dispersed by the dispersive medium. In imaging the eye, the wavelengths of the light beam are preferably in the range of 500 nm to 1200 nm, or in the range of the 700 to 950 nm.

The portion of light beam 4 diverted to sample arm 8 proceeds along the sample arm optical path and is directed by optical element 20 towards eye 40 having a partially reflective first position 42, which is preferably selected to be at or near the anterior chamber 74 of the eye. A portion of light beam 4 is reflected at or near position 42, and a portion of the light beam continues through the eye to a second position 44 within the eye 40 near the retina 76. Light beam 4 is reflected at second position 44 as return light and is directed back towards the first position 42. The return light from the second position 44 has a higher dispersion than the return light from position 42 due to the dispersive effect of the vitreous humor on the light beam 4 as it travels from position 42 to position 44 and the dispersive effect of the vitreous humor as the return light from position 44 travels to position 42. The return light from the first position 42 and the second position 44 are collected and directed back along the sample arm optical path toward beam combiner 34 to be combined with the light beam from the reference arms.

The portion of the OCT light beam diverted to reference path 10 is further split into a first reference path 14 and a second reference path 16. The first reference path 14 comprises at least a first optical delay element 24 and a first dispersion modifying element 26. The optical delay element 24 is selected so that optical path length of the reference path is the same or substantially the same as the optical path length of the return light beam from first position 42. The first dispersion modifying element 26 is selected so the dispersion of the light from reference path 14 is the same or substantially the same as the dispersion of the reflected light from the first position 42 at the point each reaches OCT detector 36. As such, the first reference path 14 corresponds to the sample arm at the first position 42. A variety of optical delay elements and strategies are well known to those of ordinary skill in the art and can be selected by those ordinarily skilled based on the design of the individual system and application.

The second reference path 16 comprises at least a second optical delay element 28 and a second dispersion modifying element 30. The second optical delay element 28 is selected so that optical path length of the reference path is the same or substantially the same as the optical path length of the light beam at the second position 44. The second dispersion modifying element 30 is selected so the dispersion of the light from second reference path 16 is the same as the dispersion of the reflected light from the second position 44 at the point each reaches the OCT detector 36. The second reference path 16 thus corresponds to the sample arm at the second position 44 and has a higher dispersion than the dispersion of the light of the first reference path 14.

The light from the first reference path 14 is then combined with the light from the second reference path 16 by beam combiner 32, and the combined reference path beams are combined with the reflected light from positions 42 and 44 by beam combiner 34. The superposition of light from each reference arms and return light reflected from each of positions 42 and 44 results in a spectral interference of the superimposed light. The OCT detector detects (i.e., measures) the resulting spectral interferogram, and the output from the detector, the measured spectral interferogram, is supplied to a processor 48. The results can be stored in the processor 48 or displayed on display 47.

The measured spectral interferogram includes a component spectral interferogram corresponding to a spectral interference between the return light from position 42 within the eye and the return light from the corresponding reference path 14, both having the same or substantially the same dispersion. Another component spectral interferogram of the measured spectral interferogram corresponds to a spectral interferogram between the return light from position 44 and the light from the corresponding second reference arm 16, both having the same dispersion that is higher than the dispersion of the other paths. As is obvious to one ordinarily skilled, the described construction provides for a measured OCT spectral interferogram comprising component spectral interference spectra corresponding positions 42 and 44, each encoded according to their respective dispersion properties. According to the present invention, these component interference spectra are obtained from the measured spectral interferogram based upon the difference in dispersion between the reflected light from positions 42 and 44 as disclosed further herein.

The systems and methods described herein therefore provide for simultaneously imaging a sample at multiple-depths within the sample. More specifically, the systems and methods described herein provide for the simultaneous imaging at multiple depths within the human eye. In preferred embodiments, the first position to be imaged within the eye is at or near the anterior surface of the lens and the second position to be imaged within the eye is at or near the retina. Thus, the OCT system and method according to the present invention makes it possible to simultaneously image both a region at or near the anterior chamber of the eye and a position at or near the retina.

Figure 4:
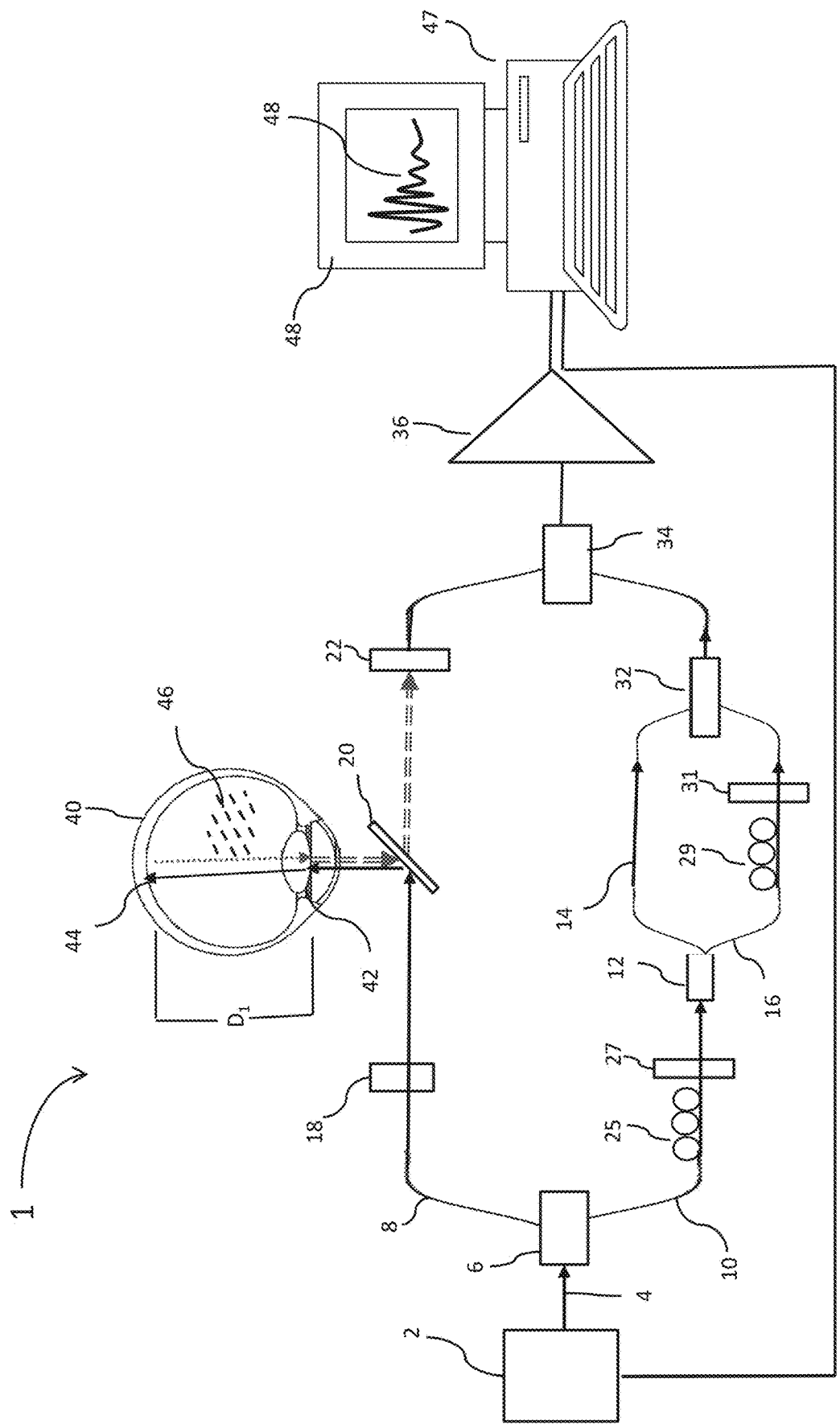
FIG. 4 is a schematic diagram of a third embodiment of a multiple depth optical coherence tomography system.

FIG. 4 is the same as FIG. 3 except for the design of the reference arm 10. In FIG. 4, a first optical delay element 25 and a first dispersion modifying element 27 are placed in the optical path of reference arm 10 prior to the beam splitter 12. In FIG. 4, the first optical delay element 25 is selected so that optical path length of the reference path is the same or substantially the same as the optical path length of the light beam to the first position 42 and the optical path length of the reflected light to the OCT detector 36. The first dispersion modifying element 27 is selected so the dispersion of the light from first reference path 14 is the same or substantially the same as the dispersion of the reflected light from the first position 42 at the point the reflected light reaches the OCT detector 36. The light of reference path 10 is then split by beam splitter 12. Here, the second reference path 16 comprises a second optical delay element 29 and a second dispersion modifying element 31. In the embodiment of FIG. 4, the second dispersion modifying element need only substantially match twice the difference in dispersion between position 42 and 44, which may simplify design and modification of the system.

Figure 5:
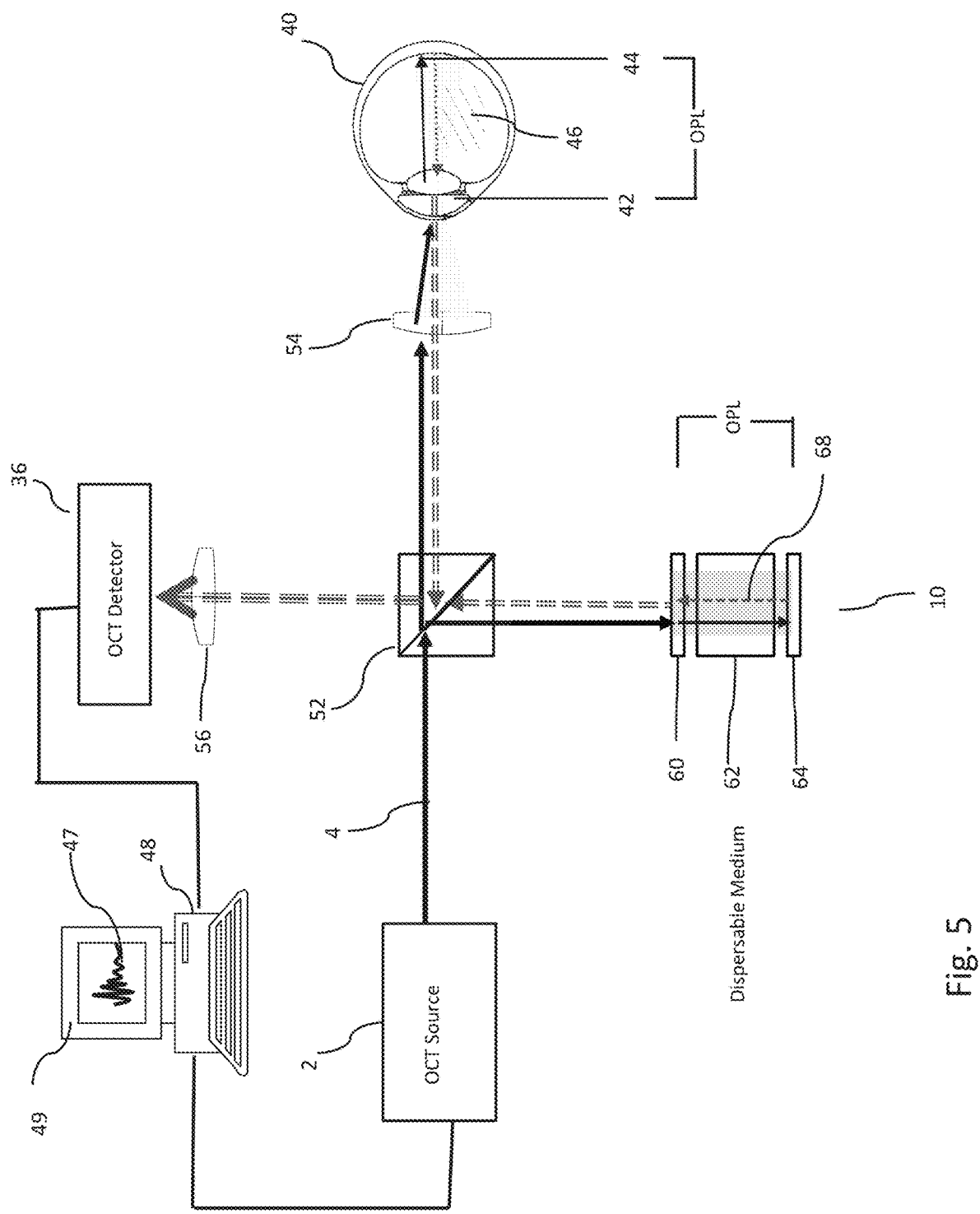
FIG. 5 is a schematic diagram of a fourth embodiment of a multiple depth optical coherence tomography system.

Another embodiment of the multi-depth OCT system and method is shown in FIG. 5. In the embodiment of FIG. 5, the sample arm comprises an objective lens 54 for focusing light beam 4 on the eye 40. In FIG. 5, OCT light source 2 produces light beam 4 directed to beam splitter 52, which diverts a portion of light beam 4 along a sample arm and a portion of light beam 4 along a reference arm. After passing through beam splitter 52, a portion of light beam 4 proceeds along the sample arm and is focused on eye 40 by objective lens 54. A portion of light beam 4 is reflected at or near position 42 within the eye, which is preferably at or near the anterior chamber, and a portion of light beam 4 proceeds past position 42 to depth position 44 within the eye 40, which is preferably at or near the retina. A portion of the light beam 4 is also reflected at or near position 44 back toward the entrance of the eye 40. The collected return light from each of position 42 and position 44 are then directed back along the sample arm through objective lens 54 and are then directed by the beam splitter 52.

Since the light beam 4 passes through the vitreous humor as it proceeds from position 42 to position 44 and the reflected beam from position 44 returns through the vitreous humor, the return beam has a higher dispersion than the return beam reflected from position 42.

The reference arm comprises a partial mirror 60, a dispersive medium 62 and a mirror 64. The portion of OCT light beam 4 diverted by beam splitter 52 along the reference arm is directed to partial mirror 60. A first portion of the incident light on partial mirror 60 is reflected from the surface of the partial mirror 60 back along the reference arm. A second portion of the incident light beam 4 passes through partial mirror 60 and is directed to mirror 64 through dispersive medium 62. The portion of light beam 4 incident on mirror 64 is then reflected back along the reference arm and through the partial mirror 60. The light reflected from mirror 64 and partial mirror 60 is returned along the reference arm to the beam splitter 52. The optical path from beam splitter 52 to partial mirror 60 and the optical path of the return light from partial mirror 60 to beam splitter 52 together define a first reference arm that corresponds to the first sample arm optical path at position 42 within the eye 40. The optical path from beam splitter 52 to mirror 64 and the optical path of reflected light from mirror 64 to beam splitter 52 together define a second reference arm that corresponds to the second sample arm optical path at position 44 in the eye 40. In a preferred embodiment, the reflecting face of the partial mirror 60 and the reflecting face of mirror 64 are parallel in a direction perpendicular to the direction of propagation of the OCT light beam.

In the embodiment of FIG. 5, the optical path length and dispersion of the first reference arm are the same or substantially the same as the optical path length and dispersion of the first sample arm optical path. The optical path length and dispersion of the second reference arm are the same or substantially the same as the optical path length and dispersion of the second sample arm optical path. In the embodiment of FIG. 5, the optical path length between the partial mirror 60 and the mirror 64 should be the same or substantially the same as the optical path length between positions 42 and position 44. Similarly, the dispersive effect of the dispersive medium 62 should be the same or substantially the same as the dispersive effect of the vitreous humor 46 between positions 42 and 44.

The return light reflected from mirror 64 is combined with the return light from the partial mirror 60, and the combined return light reflected from positions 42 and 44 are directed to the OCT detector 36 by beam splitter 52. The superposition of light from the return light reflected from partial mirror 64, the light reflected from partial mirror 60 and the return light reflected from each of positions 42 and 44 results in a spectral interference of the superimposed light. The OCT detector detects (i.e., measures) spectral interferogram, and the output from the detector, the measured spectral interferogram, is supplied to a processor 48. The results can be stored in the processor 48 or displayed on display 47.

The measured spectral interferogram includes a component spectral interferogram corresponding to a spectral interference between the return light from position P1 and the return light from the corresponding return light from partial mirror 60, both having the lower dispersion. Another component element of the measured spectral interferogram corresponds to a spectral interferogram between the return light from position P2 and the light from the mirror, both having the higher dispersion. As is obvious to one ordinarily skilled, the described construction provides for a measured OCT spectral interferogram comprising component spectral interference spectra corresponding to each of the positions within the sample to be imaged, each encoded according to their respective dispersion properties. According to the present invention, these component interference spectra are derived from the measured spectral interferogram based upon the difference in dispersion between the respective positions to be imaged as is described in more detail herein.

The OCT system and method described herein can be implemented as part of a laser eye surgery system incorporated into laser eye surgery methods. The type of laser eye surgery system and methods that may incorporate the laser eye surgery system and method is not particularly limited.

Figure 7A:
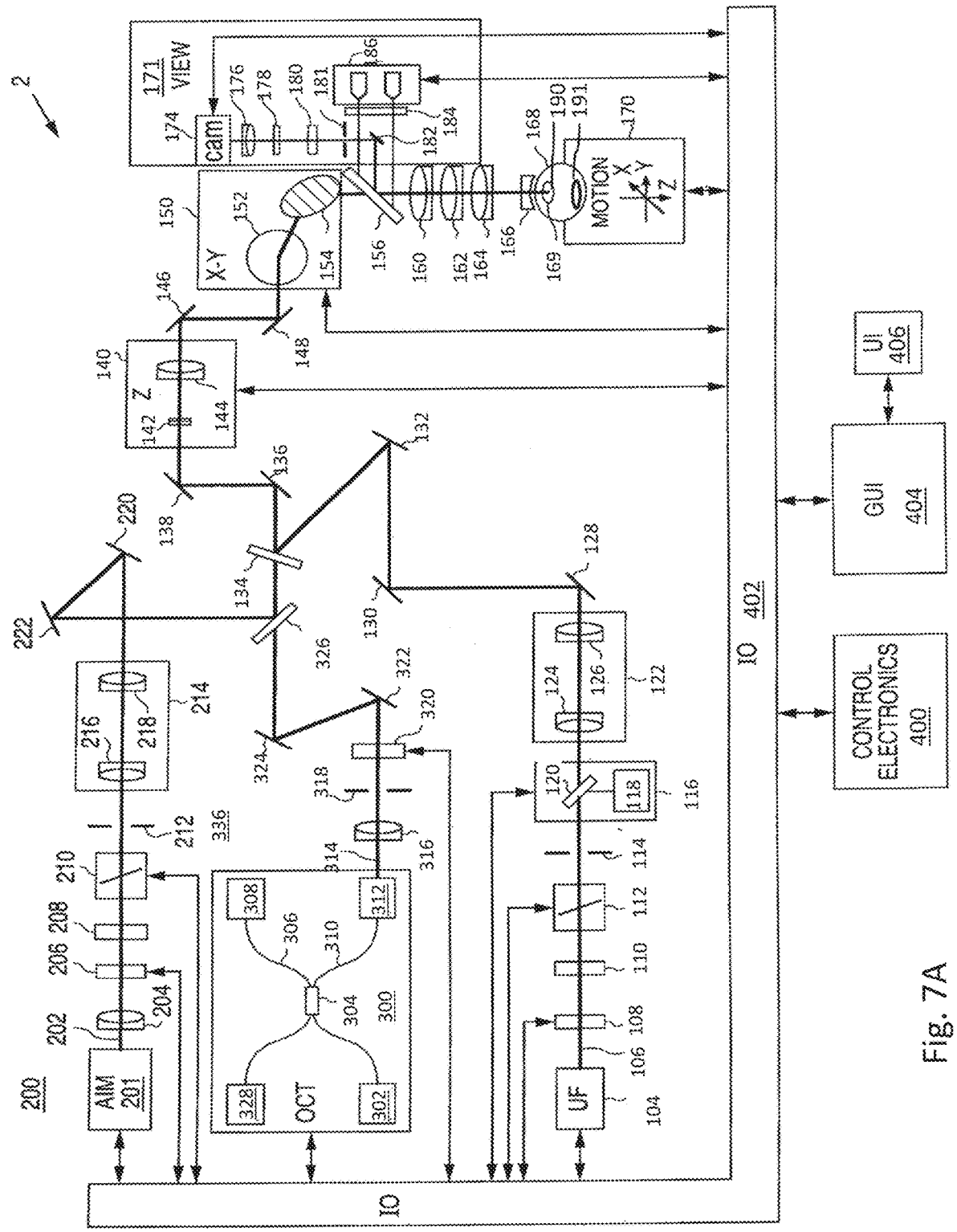
FIG. 7A is a schematic diagram of the laser surgical system incorporating the multiple depth optical coherence tomography system.

One such example is shown in FIG. 7A. The laser eye surgery system projects or scans an optical beam into a patient's eye 168. It includes an ultrafast (UF) light source 104 (e.g., a femtosecond laser, or a dual purpose system capable of emitting pulses in a lower and in a higher range of pulse energies, perhaps with different pulse durations). Using this system, a beam may be scanned in a patient's eye in three dimensions: X, Y, and Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 168 and specifically within the crystalline lens 169 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 104 may be a repetitively pulsed at 1035 nm in a device that produces 500 fs pulses at a repetition rate of 100 kHz, and an individual pulse energy in the ten microjoule range. Although not illustrated, UF Light Source 104 may be further configured to provide higher energy pulses with the same or longer pulse durations than those exiting the system after pulse compression. That is, the un-compressed beam may be extracted from UF Light Source 4 in order to provide those higher energy pulses. Regardless, the following system description details means to achieve the usage of higher and/or lower energy pulses.

The laser 104 is controlled by control electronics 400, via an input and output device 302, to create optical beam 106. Control electronics 400 may be a computer, microcontroller, etc. In this example, the entire system is controlled by the controller 400, and data moved through input/output device IO 402. A graphical user interface GUI 404 may be used to set system operating parameters, process user input (UI) 406 on the GUI 404, and display gathered information such as images of ocular structures.

The generated UF light beam 106 proceeds towards the patient eye 168 passing through half-wave plate, 108, and linear polarizer, 110. The polarization state of the beam can be adjusted so that the desired amount of light passes through half-wave plate 108 and linear polarizer 10, which together act as a variable attenuator for the UF beam 106. Additionally, the orientation of linear polarizer 110 determines the incident polarization state incident upon beam combiner 134, thereby optimizing beam combiner throughput.

The UF beam proceeds through a shutter 112, aperture 114, and a pickoff device 116. The system controlled shutter 112 ensures on/off control of the laser for procedural and safety reasons. The aperture sets an outer useful diameter for the laser beam and the pickoff monitors the output of the useful beam. The pickoff device 116 includes of a partially reflecting mirror 120 and a detector 118. Pulse energy, average power, or a combination may be measured using detector 118. The information can be used for feedback to the half-wave plate 8 for attenuation and to verify whether the shutter 112 is open or closed. In addition, the shutter 112 may have position sensors to provide a redundant state detection.

The beam passes through a beam conditioning stage 122, in which beam parameters such as beam diameter, divergence, circularity, and astigmatism can be modified. In this illustrative example, the beam conditioning stage 122 includes a two element beam expanding telescope comprised of spherical optics 124 and 126 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 122 can be used to image aperture 114 to a desired location (e.g., the center location between the 2-axis scanning device 150 described below). In this way, the amount of light that makes it through the aperture 114 is assured to make it through the scanning system. Pickoff device 116 is then a reliable measure of the usable light.

After exiting conditioning stage 122, beam 106 reflects off of fold mirrors 128, 130, and 132. These mirrors can be adjustable for alignment purposes. The beam 106 is then incident upon beam combiner 134. Beam combiner 134 reflects the UF beam 106 (and transmits both the OCT 314 and aim 202 beams described below). For an efficient beam combiner operation, the angle of incidence is preferably kept below 45 degrees and the polarization where possible of the beams is fixed. For the UF beam 106, the orientation of linear polarizer 110 provides fixed polarization.

Following the beam combiner 134, the beam 106 continues onto the z-adjust or Z scan device 140. In this illustrative example the z-adjust includes a Galilean telescope with two lens groups 142 and 144 (each lens group includes one or more lenses). Lens group 142 moves along the z-axis about the collimation position of the telescope. In this way, the focus position of the spot in the patient's eye 168 moves along the z-axis as indicated. In general there is a fixed linear relationship between the motion of lens 142 and the motion of the focus. In this case, the z-adjust telescope has an approximate 2× beam expansion ratio and a 1:1 relationship of the movement of lens 142 to the movement of the focus. Alternatively, lens group 144 could be moved along the z-axis to actuate the z-adjust, and scan. The z-adjust is the z-scan device for treatment in the eye 168. It can be controlled automatically and dynamically by the system and selected to be independent or to interplay with the X-Y scan device described next. Mirrors 136 and 138 can be used for aligning the optical axis with the axis of z-adjust device 140.

After passing through the z-adjust device 140, the beam 106 is directed to the x-y scan device by mirrors 146 and 148. Mirrors 146 and 148 can be adjustable for alignment purposes. X-Y scanning is achieved by the scanning device 150 preferably using two mirrors 152 and 154 under the control of control electronics 400, which rotate in orthogonal directions using motors, galvanometers, or any other well-known optic moving device. Mirrors 152 and 154 are located near the telecentric position of the objective lens 158 and contact lens 166 combination described below. Tilting these mirrors 152/154 causes them to deflect beam 106, causing lateral displacements in the plane of UF focus located in the patient's eye 168. Objective lens 158 may be a complex multi-element lens element, as shown, and represented by lenses 160, 162, and 164. The complexity of the lens 158 will be dictated by the scan field size, the focused spot size, the available working distance on both the proximal and distal sides of objective 158, as well as the amount of aberration control. An f-theta lens 158 of focal length 60 mm generating a spot size of 10 μm, over a field of 10 mm, with an input beam size of 15 mm diameter is an example. Alternatively, X-Y scanning by scanner 150 may be achieved by using one or more moveable optical elements (e.g., lenses, gratings) which also may be controlled by control electronics 400, via input and output device 402.

The aiming and treatment scan patterns can be automatically generated by the scanner 150 under the control of controller 400. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 106), but preferably at least defines its boundaries in order to ensure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 166, which can be any suitable ophthalmic lens, can be used to help further focus the optical beam 106 into the patient's eye 168 while helping to stabilize eye position. The positioning and character of optical beam 106 and/or the scan pattern the beam 106 forms on the eye 168 may be further controlled by use of an input device such as a joystick, or any other appropriate user input device (e.g., GUI 404) to position the patient and/or the optical system.

The UF laser 104 and controller 400 can be set to target the surfaces of the targeted structures in the eye 168 and ensure that the beam 106 will be focused where appropriate and not unintentionally damage non-targeted tissue. Other imaging modalities and techniques described herein, such as for example, Purkinje imaging, Scheimpflug imaging, or ultrasound may also be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 6A, an OCT device 300 is described, although other modalities may be included within the scope of the present invention. In the context of a laser surgical system including the multiple depth OCT system described herein, the OCT scan of the eye at a preferred first depth will provide information about the axial location of the anterior and posterior lens capsule, the boundaries of the cataract nucleus, as well as the depth of the anterior chamber. A preferred second depth will provide information regarding the axial length of the eye and the retina. This information is then be loaded into the control electronics 400, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 300 in FIG. 7A includes a broadband or a swept light source 302 that is split by a fiber coupler 304 into a reference arm 306 and a sample arm 310. The reference arm 306 includes a module 308 comprising one of the reference arms arrangements shown in FIGS. 6B and 6C containing a reference reflection for each position 190, 191 in the eye to be imaged along with suitable dispersion and path length compensation for each position. The sample arm 310 of the OCT device 300 has an output connector 312 that serves as an interface to the rest of the UF laser system. The return signals from both the reference and sample arms 306, 310 are then directed by coupler 304 to a detection device 328, which employs either time domain, frequency or single point detection techniques. In FIG. 7A, a frequency domain technique is used with an OCT wavelength of 920 nm and bandwidth of 100 nm.

Figure 7B:
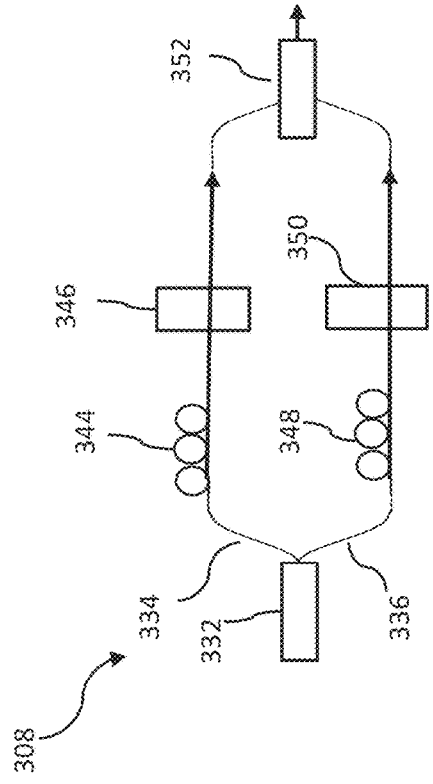
FIG. 7B is a schematic diagram of one embodiment of the reference arm module of the laser surgical system of FIG. 7A.

In FIG. 7B, the OCT reference arm 306 is split into two additional reference arm paths 334 and 336. Reference arm path 334 comprising an optical path length modifier 344 and dispersion modifier 346 so that the optical path length of reference arm path 334 corresponds to the position 190 to be imaged. Reference arm path 336 comprising an optical path length modifier 348 and dispersion modifier 350 so that the optical path length of reference arm path 336 corresponds to the position 191 to be imaged. Reference arm paths 334 and 336 are then combined by beam combiner 352 and the combined beam is returned along return path 306.

Figure 7C:
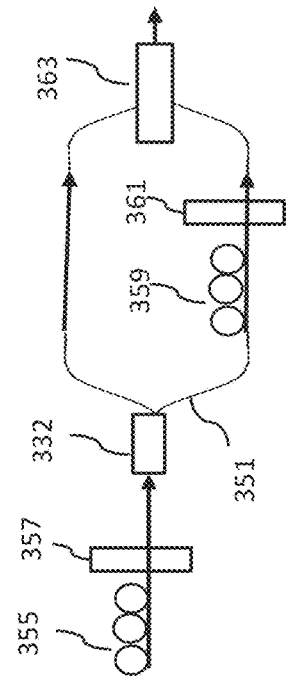
FIG. 7C is a schematic diagram of one embodiment of the reference arm module of the laser surgical system of FIG. 7A.

In FIG. 7C, the OCT reference arm 306 comprises an optical path length modifier 344 and dispersion modifier 346 so that the optical path length of the reference arm corresponds to the position 190 to be imaged. Thereafter, the reference arm path is split, and reference arm path 351 comprising an optical path length modifier 359 and dispersion modifier 361 so that the optical path length of reference arm path 351 corresponds to the position 191 to be imaged. The reference arm paths then combined by beam combiner 352 and the combined beam is returned along return path 306.

Exiting connector 312, the OCT beam 314 of the sample arm is collimated using lens 316. The size of the collimated beam 314 is determined by the focal length of lens 316. The size of the beam 314 is dictated by the desired NA at the focus in the eye and the magnification of the beam train leading to the eye 168. Generally, OCT beam 314 does not require as high an NA as the UF beam 106 in the focal plane and therefore the OCT beam 314 is smaller in diameter than the UF beam 106 at the beam combiner 134 location. Following collimating lens 316 is aperture 318 which further modifies the resultant NA of the OCT beam 314 at the eye. The diameter of aperture 318 is chosen to optimize OCT light incident on the target tissue and the strength of the return signal. Polarization control element 320, which may be active or dynamic, is used to compensate for polarization state changes which may be induced by individual differences in corneal birefringence, for example. Mirrors 322 & 324 are then used to direct the OCT beam 314 towards beam combiners 326 & 134. Mirrors 322 & 324 may be adjustable for alignment purposes and in particular for overlaying of OCT beam 314 to UF beam 106 subsequent to beam combiner 134. Similarly, beam combiner 326 is used to combine the OCT beam 314 with the aim beam 202 described below.

Once combined with the UF beam 106 subsequent to beam combiner 134, OCT beam 314 follows the same path as UF beam 106 through the rest of the system. In this way, OCT beam 314 is indicative of the location of UF beam 106. OCT beam 314 passes through the z-scan 140 and x-y scan 150 devices then the objective lens 158, contact lens 166 and on into the eye 168. Reflections and scatter off of structures at or near a first position 190 and at or near a second position 191 within the eye provide return beams that retrace back through the optical system, into connector 312, through coupler 304, and to OCT detector 328. These return back reflections provide the OCT signals that are in turn interpreted by the system as to the location in X, Y Z of UF beam 106 focal location.

It should be noted that passing the OCT through z-adjust 140 alter the z-range of OCT system 300 because the optical path length does not change as a function of movement of 42. OCT system 300 has an inherent z-range at each position that is related to the detection scheme, and in the case of frequency domain detection it is specifically related to the spectrometer and the location of the reference arm 306. In the case of OCT system 300 used in FIG. 7A, the z-range at each position is approximately 1-2 mm in an aqueous environment at each position, which may be extended up to about 4 mm at each position. Passing the OCT beam 314 in the sample arm through the z-scan of z-adjust 140 allows for optimization of the OCT signal strength. This is accomplished by focusing the OCT beam 314 onto the targeted structure while accommodating the extended optical path length by commensurately increasing the path within the reference arm 306 of OCT system 300.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 106 in the focal plane and therefore aim beam 202 is of similar diameter to the UF beam at the beam combiner 34 location. Because the aim beam is meant to stand-in for the UF beam 106 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beam combiners 326 and 34, thereby fixing the polarization state and allowing for optimization of the beam combiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well-known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 106 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 114.

The aim beam 202 next reflects off of fold mirrors 222 & 220, which are preferably adjustable for alignment registration to UF beam 106 subsequent to beam combiner 34. The aim beam 202 is then incident upon beam combiner 326 where the aim beam 202 is combined with OCT beam 314. Beam combiner 326 reflects the aim beam 202 and transmits the OCT beam 314, which allows for efficient operation of the beam combining functions at both wavelength ranges. Alternatively, the transmit and reflect functions of beam combiner 326 can be reversed and the configuration inverted. Subsequent to beam combiner 326, aim beam 202 along with OCT beam 314 is combined with UF beam 106 by beam combiner 134.

A device for imaging the target tissue on or within the eye 168 is shown schematically in FIG. 6A as imaging system 171. Imaging system includes a camera 174 and an illumination light source 186 for creating an image of the target tissue. The imaging system 171 gathers images which may be used by the system controller 400 for providing pattern centering about or within a predefined structure. The illumination light source 186 for the viewing is generally broadband and incoherent. For example, light source 186 can include multiple LEDs as shown. The wavelength of the viewing light source 186 is preferably in the range of 700 nm to 750 nm, but can be anything that is accommodated by the beam combiner 156, which combines the viewing light with the beam path for UF beam 106 and aim beam 202 (beam combiner 156 reflects the viewing wavelengths while transmitting the OCT and UF wavelengths). The beam combiner 156 may partially transmit the aim wavelength so that the aim beam 202 can be visible to the viewing camera 174. Optional polarization element 184 in front of light source 186 can be a linear polarizer, a quarter wave plate, a half-wave plate or any combination, and is used to optimize signal. A false color image as generated by the near infrared wavelength is acceptable.

The illumination light from light source 186 is directed down towards the eye using the same objective lens 158 and contact lens 166 as the UF and aim beam 106, 202. The light reflected and scattered off of various structures in the eye 168 are collected by the same lenses 158 & 166 and directed back towards beam combiner 156. There, the return light is directed back into the viewing path via beam combiner and mirror 182, and on to camera 174. Camera 174 can be, for example but not limited to, any silicon based detector array of the appropriately sized format. Video lens 176 forms an image onto the camera's detector array while optical elements 180 & 178 provide polarization control and wavelength filtering respectively. Aperture or iris 181 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 171.

Coarse adjust registration is usually needed so that when the contact lens 166 comes into contact with the cornea, the targeted structures are in the capture range of the X, Y scan of the system. Therefore a docking procedure is preferred, which preferably takes in account patient motion as the system approaches the contact condition (i.e. contact between the patient's eye 168 and the contact lens 166. The viewing system 171 is configured so that the depth of focus is large enough such that the patient's eye 168 and other salient features may be seen before the contact lens 166 makes contact with eye 168.

Preferably, a motion control system 170 is integrated into the overall control system, and may move the patient, the system or elements thereof, or both, to achieve accurate and reliable contact between contact lens 166 and eye 168. Furthermore, a vacuum suction subsystem and flange may be incorporated into the system, and used to stabilize eye 168. The alignment of eye 168 to the system via contact lens 166 may be accomplished while monitoring the output of imaging system 171, and performed manually or automatically by analyzing the images produced by imaging system 171 electronically by means of control electronics 400 via IO 402. Force and/or pressure sensor feedback may also be used to discern contact, as well as to initiate the vacuum subsystem.

An alternative beam combining configuration is shown in the alternate embodiment of FIG. 2. For example, the passive beam combiner 134 in FIG. 1 can be replaced with an active combiner, which can be a moving or dynamically controlled element such as a galvanometric scanning mirror. Active combiner changes it angular orientation in order to direct either the UF beam or the combined aim and OCT beams towards the scanner 150 and eventually eye 168 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 8A:
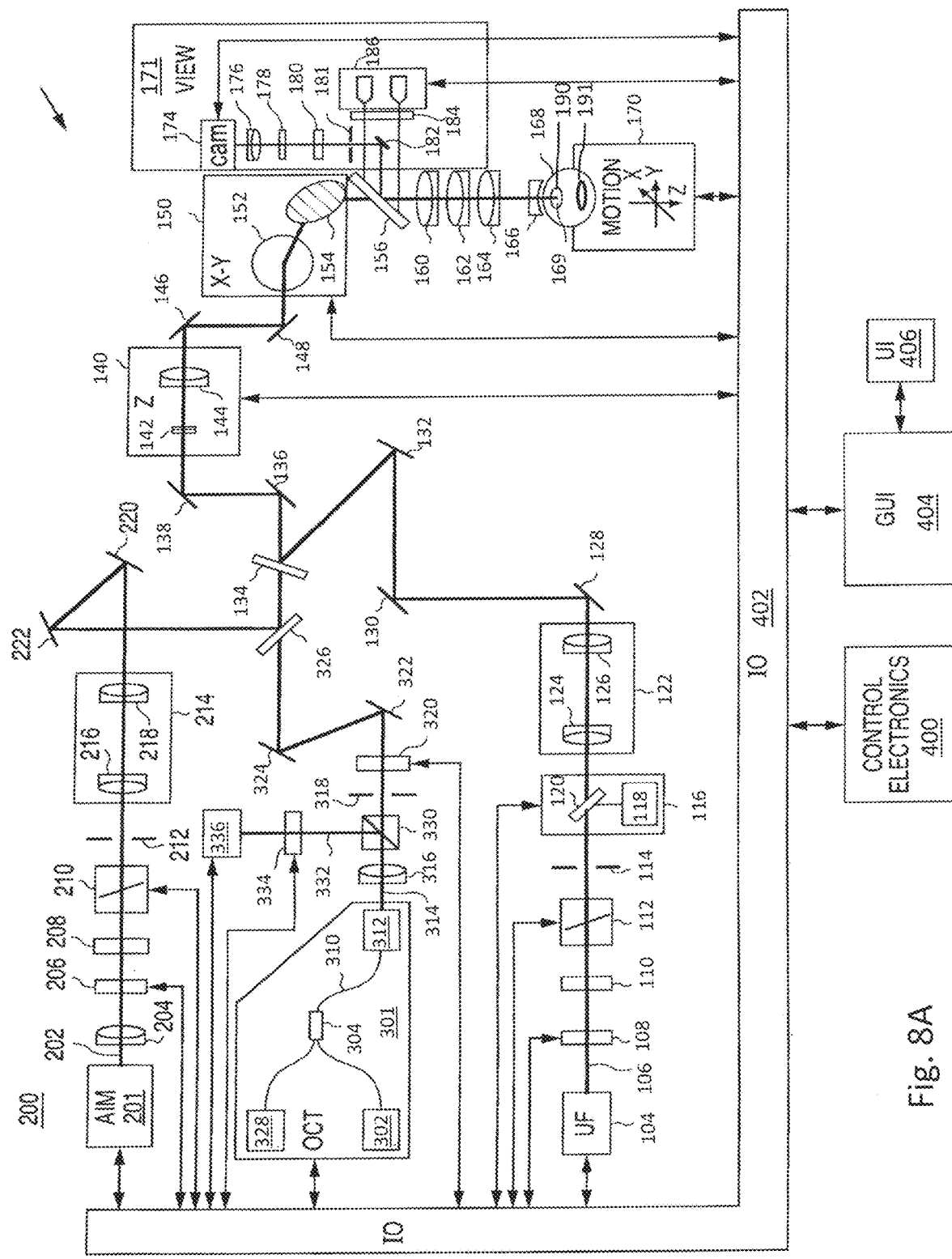
FIG. 8A is a schematic diagram of the optical beam scanning system with an alternative OCT configuration.
Figure 8B:
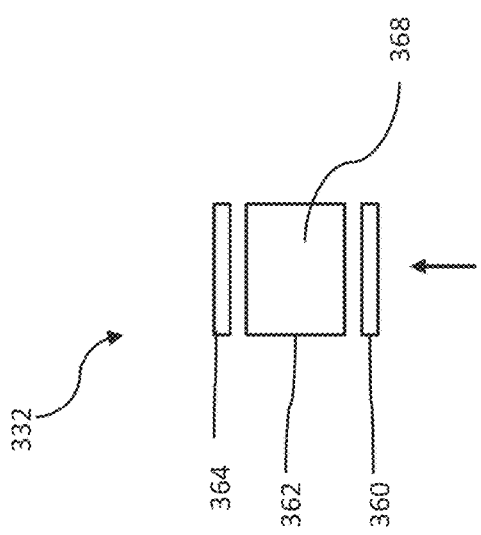
FIG. 8B is a schematic diagram of the OCT reference arm module of the laser surgical system of FIG. 8A.

Another alternate embodiment is shown in FIG. 8A which is similar to that of FIG. 7A but utilizes an alternate approach to OCT 300. In FIG. 8A, OCT 301 is the same as OCT 300 in FIG. 7A, except that the reference arm module 306 has been replaced by reference arm 332. This free-space OCT reference arm module 332 is realized by including beam splitter 330 after lens 316. The reference beam 332 then proceeds through polarization controlling element 334 and then onto the reference return module 336. The reference return module 336 contains the appropriate dispersion and path length adjusting and compensating elements and generates an appropriate reference signal for imaging position 190 and 191 within the eye for interference with the sample signal. As shown in FIG. 8B, reference arm module 332 comprises a partial mirror 360 and mirror 364 and a dispersive medium 368 therebetween. Return light reflected of partial mirror 60 corresponds to position 190 to be imaged and return light reflected from mirror 364 corresponds to position 191 to be imaged. The sample arm of OCT 300 now originates subsequent to beam splitter 330. The potential advantages of this free space configuration include separate polarization control and maintenance of the reference and sample arms. The fiber based beam splitter 304 of OCT 300 can also be replaced by a fiber based circulator. Alternately, both OCT detector 328 and beam splitter 330 might be moved together as opposed to reference arm 336.

The laser surgical system, including the OCT system and methods described herein, may be used in connection with a method of treating a lens of a patient's eye includes generating a light beam, deflecting the light beam using a scanner to form a treatment pattern of the light beam, delivering the treatment pattern to the lens of a patient's eye to create a plurality of cuts in the lens in the form of the treatment pattern to break the lens up into a plurality of pieces, and removing the lens pieces from the patient's eye.

The laser surgical system, including the OCT system and methods described herein, may also be used in connection to a method of treating a lens of a patient's eye that includes generating a light beam, deflecting the light beam using a scanner to form a treatment pattern of the light beam, delivering the treatment pattern to the lens of a patient's eye to create a plurality of cuts in the lens in the form of the treatment pattern, mechanically breaking the lens into a plurality of pieces along the cuts, and removing the lens pieces from the patient's eye.

It is to be understood that the present invention is not limited to the embodiment(s) described above and illustrated herein, but encompasses any and all variations explicitly and implicitly derived therefrom. For example, the lens conditioning may be made in multiple steps, with the capsulotomy occurring between them to accomplish the intended goal. Although not shown in the figures, multiple imaging steps can also be employed in between treatment steps to account for any changes in position and/or size due to treatment and further insure the accurate disposition of laser energy in the target tissue All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A multiple depth optical coherence tomography (OCT) system for imaging positions at multiple depth positions in an object, the OCT system comprising:
    a light source for providing a beam of light;
    a beam splitter disposed to receive the beam of light from the light source and split the beam of light into a sample light and a reference light;
    a beam combiner;
    an OCT detector;
    a sample arm configured to propagate the sample light from the beam splitter to the object and to direct an object return light from the object to the beam combiner, the object return light comprising a first return light beam reflected from a first position in the object and a second return light beam reflected from a second position in the object, the first position and the second position being at different depths in the object located along a common axis, the first return light beam and the second return light beams being superimposed on each other, the second return light having a second dispersion level that is larger than a first dispersion level of the first return light beam by a dispersion difference amount;
    a first reference arm configured to propagate a first portion of the reference light from the beam splitter to the beam combiner with a third dispersion level that is substantially the same as the first dispersion level; and
    a second reference arm configured to propagate a second portion of the reference light from the beam splitter to the beam combiner with a fourth dispersion level that is substantially the same as the second dispersion level;
    wherein the beam combiner is configured to combine the object return light including the first return light beam and the second return light beam, the first portion of the reference light, and the second portion of the reference light to superimpose them into one combined beam, and to direct the combined beam along a single common optical path to the OCT detector; and
    wherein the OCT detector is configured to receive the combined beam, to measure an interferogram based on the combined beam, and to obtain imaging information for both the first position and the second position from the interferogram based on the dispersion difference amount.

2. The multiple depth OCT system of claim 1, wherein a distance between the first position and the second position is more than 5 mm or more than 10 mm.

3. The multiple depth OCT system of claim 1, wherein the object is an eye, wherein the first position is at or near an anterior chamber of the eye, and wherein the second position is located posterior to the anterior chamber of the eye.

4. The multiple depth OCT system of claim 3, wherein the second position is located at or near the retina.

5. The multiple depth OCT system of claim 1, wherein the first reference arm comprises a partial mirror, the second reference arm comprises a mirror and a dispersive medium disposed between the partial mirror and the mirror, wherein an optical path length difference between the first position and the second position in the object is substantially the same as an optical path length between the reference arm partial mirror and the reference arm mirror, and wherein the dispersive medium of the second reference arm has a dispersion level that is substantially the same as the dispersion difference amount.

6. A laser surgical system comprising:
    the multiple depth OCT system according to claim 1.

7. The multiple depth OCT system of claim 1, wherein the OCT detector is configured to separate two component spectral interferograms from one another in the measured interferogram based on the dispersion difference amount, and to obtain imaging information for both the first position and the second position based on the two component spectral interferograms.

8. The multiple depth OCT system of claim 1, wherein the first reference arm and the sample arm for the first position in the object have substantially the same optical path lengths, and the second reference arm and the sample arm for the second position in the object have substantially the same optical path lengths.

9. The multiple depth OCT system of claim 1, wherein the beam combiner and the beam splitter is a common optical element.

10. A multiple-depth Optical Coherence Tomography (OCT) method for imaging an object, the OCT system comprising:
dividing a beam of light into a sample portion and a reference portion;
directing the sample portion along a sample arm optical path to the object and directing object return light along the sample arm optical path to a beam combiner, the object return light comprising a first return light beam reflected from a first position in the object and a second return light beam reflected from a second position in the object, the first position and the second position being at different depths in the object located along a common axis, the first return light beam and the second return light beams being superimposed on each other, the second return light having a second dispersion level that is larger than a first dispersion level of the first return light beam by a dispersion difference amount;
directing a first portion of the reference portion along a first reference arm to the beam combiner to produce a first reference light beam with a third dispersion level that is substantially the same as the first dispersion level;
directing a second portion of the reference portion along a second reference arm to the beam combiner to produce a second reference light beam with a fourth dispersion level that is substantially the same as the second dispersion level;
by the beam combiner, combining the object return light including the first return light beam and the second return light beam, the first reference light beam, and the second reference light beam to superimpose them into one combined beam, and directing the combined beam along a single common optical path to an OCT detector; and
by the OCT detector, receiving the combined beam, measuring an interferogram based on the combined beam, and obtaining imaging information for both the first position and the second position from the interferogram based on the dispersion difference amount.

11. The multiple depth OCT method of claim 10, wherein a distance between the first position and the second position is more than 5 mm or more than 10 mm.

12. The multiple depth OCT method of claim 10, wherein the object is an eye, wherein the first position is at or near anterior chamber of the eye, and wherein the second position is located posterior to the anterior chamber of the eye.

13. The multiple depth OCT method of claim 12, wherein the second position is located at or near the retina.

14. The multiple depth OCT method of claim 10, wherein the first reference arm comprises a partial mirror, the second reference arm comprises a mirror and a dispersive medium disposed between the partial mirror and the mirror, wherein an optical path length difference between the first position and the second position in the object is substantially the same as an optical path length between the reference arm partial mirror and the reference arm mirror, and wherein the dispersive medium of the second reference arm has a dispersion level that is substantially the same as the dispersion difference amount.

15. The multiple depth OCT method of claim 10, wherein the step of obtaining the imaging information for both the first position and the second position based on the dispersion difference amount includes:
separating two component spectral interferograms from one another in the measured interferogram based on the dispersion difference amount; and
obtaining imaging information for both the first position and the second position based on the two component spectral interferograms.

16. The multiple depth OCT method of claim 10, wherein the first reference arm and the sample arm for the first position in the object have substantially the same optical path lengths, and the second reference arm and the sample arm for the second position in the object have substantially the same optical path lengths.

17. A multiple depth optical coherence tomography (OCT) system for imaging positions at multiple depth positions in a sample, the OCT system comprising:
a light source for providing a beam of light;
a beam splitter disposed to receive the beam of light from the light source and split the beam of light into a sample light and a reference light;
a beam combiner;
an OCT detector;
a sample arm configured to propagate the sample light from the beam splitter to the object and to direct an object return light from the object to the beam combiner, the object return light comprising a first return light beam reflected from a first position in the object and a second return light beam reflected from a second position in the object, the first position and the second position being at different depths in the object located along a common axis, the first return light beam and the second return light beams being superimposed on each other, the second return light having a second dispersion level that is larger than a first dispersion level of the first return light beam by a dispersion amount;
a reference arm comprising a partial mirror, a mirror, and a dispersive medium between the partial mirror and the mirror, the partial mirror configured to reflect a first portion of the reference light to produce, at the beam combiner, a first reference light beam having a third dispersion level that is substantially the same as the first dispersion level, and the mirror configured to reflect a second portion of the reference light to that has passed through the dispersive medium to produce, at the beam combiner, a second reference light beam having a fourth dispersion level that is substantially the same as the second dispersion level; and
wherein the beam combiner is configured to combine the object return light including the first return light beam and the second return light beam, the first reference light beam, and the second reference light beam to superimpose them into one combined beam, and to direct the combined beam along a single common optical path to the OCT detector; and
wherein the OCT detector is configured to receive the combined beam, to measure an interferogram based on the combined beam, and to obtain imaging information for both the first position and the second position from the interferogram based on the dispersion difference amount.

18. The multiple depth OCT system of claim 17, wherein a distance between the first position and the second position is more than 5 mm or more than 10 mm.

19. The multiple depth OCT system of claim 17, wherein the OCT detector is configured to separate two component spectral interferograms from one another in the measured interferogram based on the dispersion difference amount, and to obtain imaging information for both the first position and the second position based on the two component spectral interferograms.

20. The multiple depth OCT system of claim 17, wherein an optical path length between the reference arm partial mirror and the reference arm mirror is substantially the same as an optical path length between the first position and the second position in the object.

* * * * *